(12) United States Patent
Carter (10) Patent No.: US 9,696,244 B2
(45) Date of Patent: Jul. 4, 2017

(54) INLINE SAMPLING FOR MULTI-PHASE FLOW

(71) Applicant: Flow Systems, Inc., Berthoud, CO (US)

(72) Inventor: Michael S. Carter, Loveland, CO (US)

(73) Assignee: Western Energy Support and Technology, Inc, Loveland, CO (US)

( * ) Notice: Subject to any disclaimer, the term of this patent is extended or adjusted under 35 U.S.C. 154(b) by 0 days.

(21) Appl. No.: 14/737,047

(22) Filed: Jun. 11, 2015

(65) Prior Publication Data

US 2016/0363226 A1  Dec. 15, 2016

(51) Int. Cl.
| | |
|---|---|
| *F16K 5/00* | (2006.01) |
| *G01N 1/22* | (2006.01) |
| *G01N 1/10* | (2006.01) |
| *F16K 5/04* | (2006.01) |
| *F16K 11/076* | (2006.01) |
| *G01N 1/20* | (2006.01) |

(52) U.S. Cl.
CPC .......... *G01N 1/2247* (2013.01); *F16K 5/0442* (2013.01); *F16K 11/076* (2013.01); *G01N 1/10* (2013.01); *G01N 1/2035* (2013.01)

(58) Field of Classification Search
CPC ..... Y10T 137/87249; Y10T 137/87362; Y10T 137/87909; F16K 27/067; G01N 1/2247
USPC .... 137/597, 599.06, 599.07, 599.13, 599.14, 137/599.15, 601.05, 625.28, 625.31, 137/625.15, 883; 73/863.73
See application file for complete search history.

(56) References Cited

U.S. PATENT DOCUMENTS

| | | | | |
|---|---|---|---|---|
| 934,614 A | * | 9/1909 | Huxley | F16K 5/0673 137/238 |
| 2,864,254 A | * | 12/1958 | McDonald | G01N 1/2035 73/863.73 |
| 3,386,461 A | * | 6/1968 | Fisher | F16K 5/10 137/237 |
| 3,884,082 A | * | 5/1975 | Merciadis | G01N 25/14 422/935 |
| 4,921,598 A | * | 5/1990 | Desch | C02F 1/42 137/599.15 |
| 5,129,420 A | * | 7/1992 | Johnson | F16K 35/14 137/595 |
| 5,467,796 A | * | 11/1995 | Pettinaroli | F16K 5/0605 134/166 C |
| 5,922,972 A | * | 7/1999 | Maurin | F16K 5/0605 73/863.57 |
| 6,200,111 B1 | * | 3/2001 | Foss | F04B 7/00 137/50 |

(Continued)

*Primary Examiner* — Reinaldo Sanchez-Medina
(74) *Attorney, Agent, or Firm* — Russell S. Krajec; Krajec Patent Offices, LLC (57) ABSTRACT

A sampling device uses two ball valves that may be operated to take a sample while allowing flow to continue in a bypass path in a pressurized pipe. As one ball valve closes, it may capture a sample of liquid and gas that may be traveling in the pipe, then the sample may be discharged through a sampling outlet. The second ball valve may be operated simultaneously to open a bypass path while the first ball valve captures a sample. In some cases, the speed of actuation may be a function of the flow speed to capture an accurate sample. In other cases, the length of pipe from the sampling valve to the bypass junction may determine the effectiveness of the sample when actuation speed is relatively slow.

19 Claims, 5 Drawing Sheets

(56) References Cited

U.S. PATENT DOCUMENTS

| | | | | |
|---|---|---|---|---|
| 6,668,860 B1 * | 12/2003 | Pas | ......................... | B01D 35/12 |
| | | | | 137/545 |
| 6,832,621 B1 * | 12/2004 | Williams | ................... | B08B 9/00 |
| | | | | 134/166 C |
| 2008/0199901 A1 * | 8/2008 | Enzien | ..................... | C12Q 1/04 |
| | | | | 435/29 |
| 2014/0299198 A1 * | 10/2014 | Diehl | .................... | F16K 11/205 |
| | | | | 137/15.01 |

* cited by examiner

INLINE SAMPLING FOR MULTI-PHASE FLOW

BACKGROUND

A typical oil and gas wellhead may product a mixture of gas, liquid, and sometimes solid material. Sampling this multi-phase material from a pressurized pipe can be difficult, as material in solid, liquid, or gaseous phases cannot be reliably extracted in proportion to their actual presence in a pipe. Specifically, the ratio of liquid to gas within the pipe can be difficult to measure using various probes, especially in high flow rates.

SUMMARY

A sampling device uses two ball valves that may be operated to take a sample while allowing flow to continue in a bypass path in a pressurized pipe. As one ball valve closes, it may capture a sample of liquid and gas that may be traveling in the pipe, then the sample may be discharged through a sampling outlet. The second ball valve may be operated simultaneously to open a bypass path while the first ball valve captures a sample. In some cases, the speed of actuation may be a function of the flow speed to capture an accurate sample. In other cases, the length of pipe from the sampling valve to the bypass junction may determine the effectiveness of the sample when actuation speed is relatively slow. The sampling valve may have an internal diameter that is similar to the internal diameter of the piping, and may capture a sample of liquid and gas that may be representative of the material flowing through the pipe when the valve is actuated.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

In the drawings,

FIG. 4 is a diagram illustration of an embodiment showing an inline sampling device with a long lead in.

DETAILED DESCRIPTION

A sampling device may use two ball values that are actuated in concert to take a sample from a pressurized pipe while allowing flow to continue uninterrupted through a bypass circuit. One ball valve may be the sampling valve that may be normally open, while the other ball valve may be the bypass value that may be normally closed. As both valves are actuated, a sample may be collected in the first valve while flow may begin to flow through the second valve. The first valve may close and completely entrap a sample of the pipe contents, while the flow may continue unimpeded through the bypass circuit. The sample may be extracted from the first valve in the closed position.

The sampling device may use full port ball valves that may have an internal diameter that is the same nominal diameter as the pipe to which it is connected. By closing the ball valve, a known volume of pipe contents can be mechanically captured within the valve cavity. The contents of the valve cavity may be removed and the contents analyzed to estimate the typical contents of the pipe.

In many oil and gas applications, a wellhead may produce both liquid and gas products, which may flow from the wellhead to a separator where the liquid and gases may flow to different processing equipment. The sampling device may be used to collect samples of wellhead flow to determine the ratio of gas to liquid. In many cases the liquid may contain both oil and water, the ratio of which can be determined by analysis of the sample. Such a ratio may be known in the industry as the "water cut". In some cases, there may be solids within the flow as well, such as sand or other materials that may be determined by further analysis.

A meaningfully accurate measurement of multi-phase material may be made by capturing a sample with a ball valve. A ball valve may have a spherical rotating ball. The ball may have an internal diameter that is the nominal diameter of a connecting pipe. When the ball is rotated to a closed position, the spherical ball may completely close the pipe, and the inside diameter of the ball may be sealed from upstream and downstream flow.

The internal cavity of the ball, when closed, may capture a volume of the contents of the pipe, including liquid, solid, and gaseous materials. The captured contents of the ball may be drained through a sampling port. In many cases, the sampling valve may also be outfitted with a pressure tap and temperature probe for measuring pressure and temperature, and a pressurization port through which argon or other gas may force the sample out through the sampling port. Some systems may include heaters or other mechanisms that may assist in removing the sample from the ball.

The sampling device may be configured with a bypass circuit. The bypass circuit may consist of a Y junction, an entry portion, the valves, an exit portion, and another junction. In some embodiments, the circuit may be lengthwise symmetrical, where the entry and exit portions being of the same length. In some embodiments, the main/bypass routes may be symmetrical such that the flow through the main portion or the bypass portion are of the same general shape and length.

The sampling device may be used in a fast acting manner. Such embodiments may have hydraulic, pneumatic, or other mechanisms that may cause the valves to operate in a relatively quickly manner, such as in a second or less. Fast acting versions may be useful for capturing flow that may be fast moving where a slow operation of the valve may disturb the flow and adversely affect the ability to collect a meaningful sample.

The sampling device may be used in a slow manner. Such embodiments may have hydraulic, pneumatic, or other mechanisms that may cause the valves to operate in a relatively slow manner, such as a second or more. In some cases, a slower acting valve may be manually actuated and may take several seconds or even minutes to actuate. Such slower closing systems may be useful in larger valves where the operation of the valve may cause water hammer or other issues, or where automated actuation systems may be cost prohibitive.

Figure 1A:
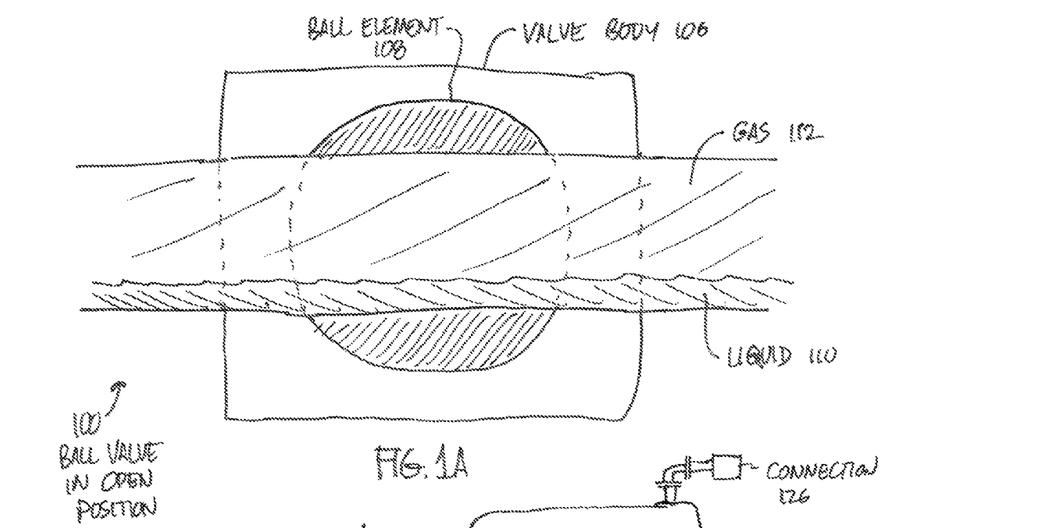
FIG. 1A is a diagram illustration of an embodiment showing a ball valve in an open position.
Figure 1B:
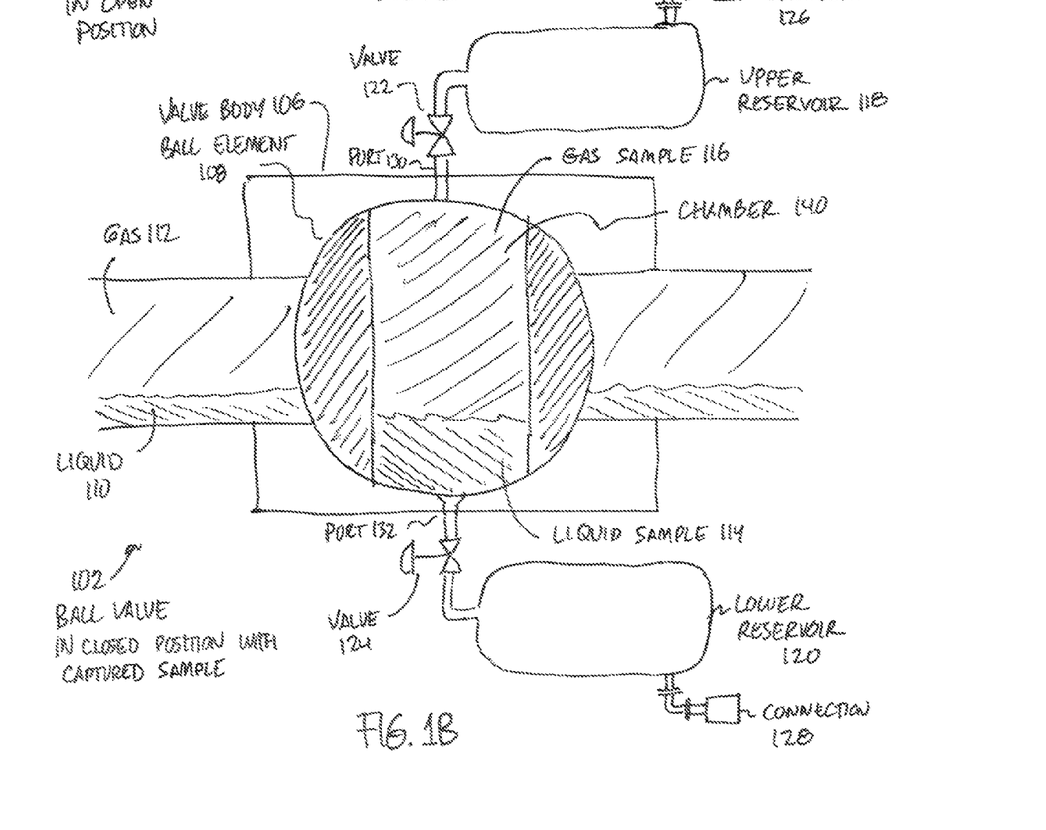
FIG. 1B is a diagram illustration of an embodiment showing a ball valve in a closed position prior to retrieving a sample.
Figure 1C:
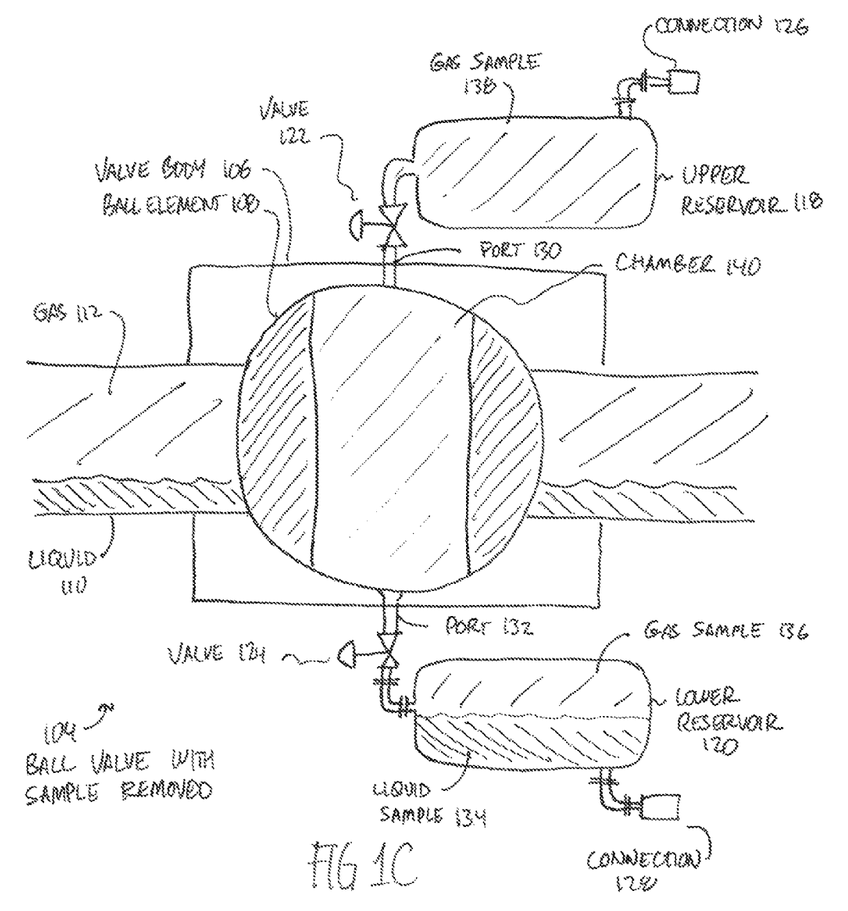
FIG. 1C is a diagram illustration of an embodiment showing a ball valve in a closed position after retrieving a sample.

FIG. 1A is a cross sectional view of an embodiment 100 showing a ball valve in an open position. FIG. 1B is a cross sectional view of an embodiment 102 showing the ball valve of embodiment 100 but in a closed position with a captured sample. FIG. 1C is a cross sectional view of an embodiment 104 of the ball valve of embodiment 102 with the sample removed.

Embodiments 100, 102, and 104 illustrate a sequence for capturing and removing a sample from piping. A ball value is used to close off flow and capture a sample, which may contain solid, liquid, and gas phase materials. The sample may be removed from the ball valve cavity as a representative content of the pipe.

The embodiments illustrate a mechanism whereby a valve that has a trapped volume may be used to collect samples from a piping system. A ball valve is used as an example because it is easily understood, although other types of valves with a trapped volume may also be used.

A ball valve may actuate by rotating a spherical ball element 108 inside a valve body 106. When the valve is open, the spherical ball element 108 may have an opening through which liquid, gas, and sometimes solid materials may flow. When the ball valve is closed, the spherical ball element 108 may rotate to stop flow. In the closed position, the opening in the valve is sealed from the upstream and downstream side of the valve, thereby entrapping a sample of the pipe contents.

In the example of embodiment 100, the ball element 108 is illustrated in the open position with respect to the valve body 106 such that there may be flow through the piping. The flow is illustrated as both liquid 110 and gas 112 components. In many cases, the liquid 110 or gas 112 components may also include solid materials.

A usage scenario for a sampling system may be to collect samples in an oil and gas application. Many wellheads may produce both a liquid and gas that may be simultaneously extracted. The liquid may contain water, oil, or other components, and the gas may be natural gas with various other gasses. A sampling system may collect samples from such flows so that an accurate measurement may be made of the ratio of liquid to gas, as well as to determine the composition of both the liquid and gas, and the amount of solids present.

In embodiment 102, the ball valve may be illustrated in the closed position with a sample captured and ready for extraction. The valve body 106 is illustrated with a ball element 108 that is closed. The liquid 110 and gas 112 from the piping may be captured in the ball element 108 as a liquid sample 114 and a gas sample 116.

In the open position as illustrated in embodiment 100, the liquid 110 and gas 112 components may flow through the valve unimpeded. In the captured position as illustrated in embodiment 102, the liquid sample 114 and the gas sample 116 may be sealed from the rest of the piping, and the samples may represent the components of the pipe contents.

With the sample trapped in embodiment 102, the valve body 106 may be outfitted with ports 130 and 132, through which the sample may be extracted. An upper reservoir 118 and lower reservoir 120 may be used to capture the sample. The upper reservoir 118 may be connected to the port 130 with a valve 122 and may have a connection 126 to receive or transmit gas or liquid. Similarly, the lower reservoir 120 may be connected to port 132 with a valve 124 and may have a connection 128 to receive or transmit gas or liquid.

The reservoirs may be used in several different scenarios to extract the captured liquid sample 114 and gas sample 116. In one scenario, the reservoirs may be evacuated then the valves 122 and 124 may be opened to extract the samples through the pressure difference. In another scenario, the upper reservoir 118 may be pressurized with argon or other gas that may not affect the sample, then the pressurized gas may be used to force the sample into the lower reservoir 120.

In some situations, heat may be applied to the valve body 106 to assist in removing a sample. Heat may be useful in helping extract very viscous liquids by improving flow, or may be useful to boil contents for extraction as a gas phase rather than liquid phase.

Embodiment 104 may illustrate the valve after a sample has been transferred to the reservoirs 118 and 120. The transfer process may occur by opening the valves 122 and 124, allowing equilibrium to be achieved, then closing valves 122 and 124. The samples may then be stored in the reservoirs 118 and 120 and may be subsequently extracted and analyzed. After the sample is removed, the valve may be opened and return to the position as illustrated in embodiment 100.

A lower port 132 may be positioned such that gravity may assist in collecting at least the liquid portion of a sample. The lower port 132 may be positioned to be at the lowest point in the cavity formed by the ball element 108. In some cases, the lower collection port may include a taper, bevel, or other feature that may assist in collecting and extracting liquid from the cavity, as well as any solids that may be entrained in the liquid.

Some embodiments may include various sensors that may probe the contents of the chamber 140, such as a pressure sensor 142 and temperature sensor 144. Such sensors may be configured to probe the chamber 140, and may be used to take measurements of a sample prior to and after removing the sample from the chamber 140.

The examples shown in FIGS. 1A, 1B, and 1C illustrate a ball valve that may oriented with a horizontal axis of rotation, with extraction ports at the top and bottom of the valve. Other embodiments may be configured with a ball valve having a vertical axis of rotation. In such an embodiment, one or more extraction port may be provided in various locations, including through a shaft along the axis of rotation. Still other embodiments may have the axis of rotation in configurations other than vertical or horizontal.

Figure 2:
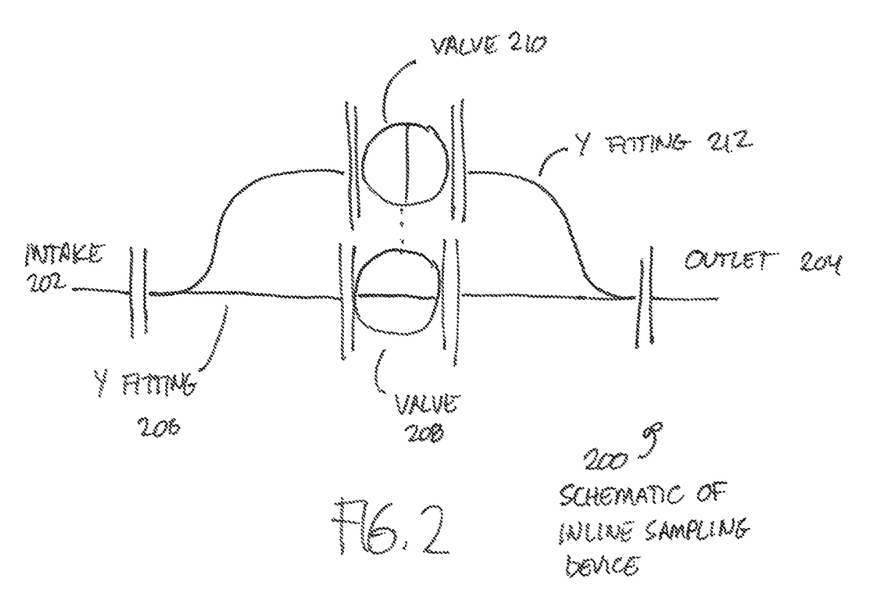
FIG. 2 is a diagram illustration of an embodiment showing a schematic of an inline sampling device.

FIG. 2 is a schematic illustration of an embodiment 200 showing an inline sampling device. An intake 202 connects to a Y fitting 206, which may connect to valves 208 and 210. A second Y fitting 212 connects the valves 208 and 210 to the outlet 204.

The valves 208 and 210 may be mechanically coupled so that one valve is open while the other valve is closed. The coupling may cause both ball elements to rotate at the same time. In some cases, the mechanical coupling may be a direct mechanical linkage such that one lever or actuation wheel may cause both valves to actuate simultaneously. In some cases, a mechanical coupling may be actuated using pneumatic, hydraulic, solenoid, or other actuators, where the actuators may be controlled by electric switch, hydraulic or pneumatic valves, automated controller, or other mechanisms.

The valves 208 and 210 may be coupled using a control system such that both valves are actuated substantially simultaneously but there may not be a mechanical linkage between the valves. In one version of such a system, a local or remote controller may cause valve 208 to open at the same time as valve 210 closes. In another version, a human operator may actuate both valves simultaneously.

The valves 208 and 210 are actuated simultaneously such that flow may continue from the intake 202 to the outlet 204 while a sample is taken. When an embodiment contains two ball valves, as one ball valve closes with a given rotational angle, the second ball valve opens the same amount. Thus, when two ball valves are mechanically coupled in embodiment 200, the cross-section area of the sum of the two valves is constant at any position of open or closed. Therefore, flow may continue from the intake 202 to the outlet 204 without impediment.

Figure 3:
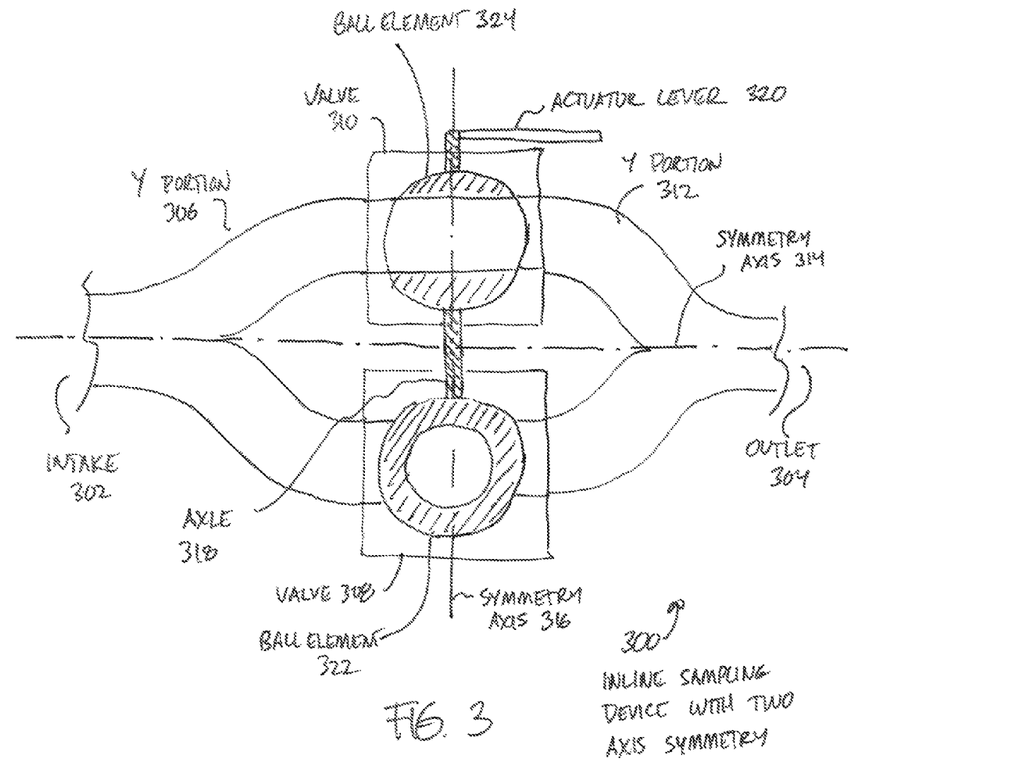
FIG. 3 is a diagram illustration of an embodiment showing a cross section of an inline sampling device with mechanical coupling and two axis symmetry.

FIG. 3 is a diagram illustration of an embodiment 300 showing an inline sampling device with two axis symmetry. Embodiment 300 illustrates a sampling system where there is symmetry between the circuits through each valve, as well as symmetry in the inlet and outlet junctions.

Embodiment 300 has an intake 302 and an outlet 304. The inlet 302 and outlet 304 are illustrated as generalized connections. In practice, a sampling device may have any type of connection to intake and output piping, such as flanged connections, threaded connections, welded connections, or any other connection type.

A Y portion 306 may connect the intake 302 to valves 308 and 310, and a second Y portion 312 may connect valves 308 and 310 to outlet 304.

The Y portions are designed to be symmetrical about a symmetry axis 314, such that flow is similar to either valve 308 or 310. In other words, flow through one valve is equivalent to flow through the other valve.

The Y portions are also designed to be symmetrical about a symmetry axis 316, such that the intake and outlet sides of the device are equivalent in length and shape.

The diagram illustration of embodiment 300 may show the device from the top, meaning that the plane of the illustration is the horizontal plane. As such, valves 308 and 310 may have a rotational axis that is horizontal and that the cavity that may capture a sample may be vertical cylinder when the valve is closed. The valve 308 is illustrated as closed with the cavity inside ball element 322 as being vertical, and the valve 310 is illustrated as open with the ball element 324 oriented to allow flow through the valve 310.

The valves 308 and 310 may be connected using an axle 318 which may mechanically couple the ball element 322 with the ball element 324. A handle or actuator lever 320 may cause the ball elements to move simultaneously, such that one motion of the actuator lever 320 may cause ball element 324 to close at the same time that ball element 322 opens, and vice versa.

The valves 308 and 310 may both be outfitted with collection reservoirs and associated valves. Such a design may enable samples to be taken from either valve when the valve is closed. An operating process may close one valve to capture a sample while the other valve opens. As the sample is retrieved from the first valve, flow may be reestablished through the second valve and the reverse actuation may capture a sample in the second valve. The second sample may be retrieved and the process may continue.

Figure 4:
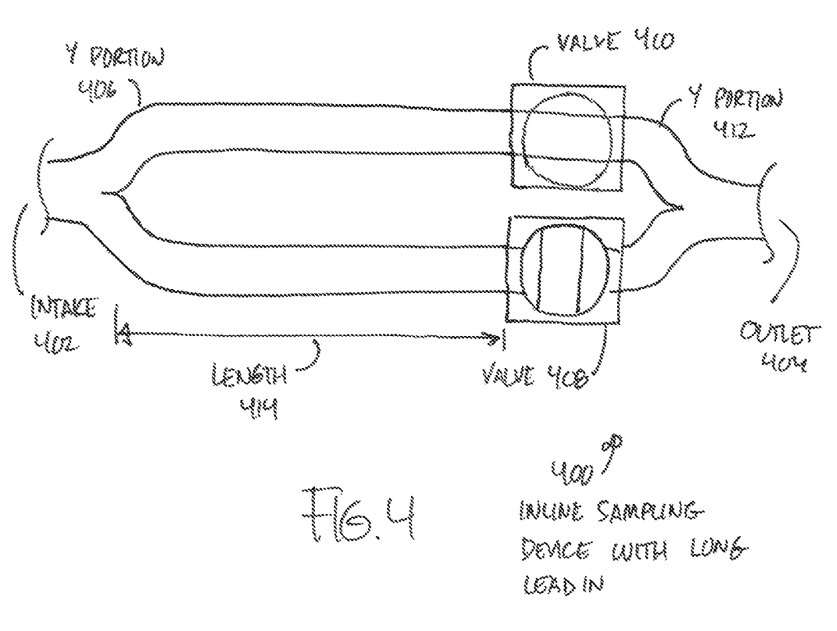

FIG. 4 is a diagram illustration of an embodiment 400 showing an inline sampling device with a long lead in. An intake 402 and outlet 404 are illustrated, with a Y portion 406 connecting the intake 402 to valves 408 and 410. A second Y portion 412 may connect the valves 408 and 410 to the outlet 404.

The Y portion 406 on the intake side may have a length 414 which may provide a long lead to the valves after the Y junctions. The length 414 may be useful in embodiments where the valves may be actuated in a relatively slow manner or in embodiments where water hammer or other effects may be present.

For example, the valves 408 and 410 may be large trunnion valves that may be operated with a hand wheel or a motorized system that may open and close the valves slowly. As the valves are being actuated, the flow in one branch or circuit of the device may slow down while flow in the other branch may begin increasing. Because a long lead in is present in the length 414, the momentum of the flow may not be as adversely affected by flow being diverted from one circuit to another while the one valve closes and the other valve opens. As such, the sample may more accurately reflect the contents of the piping. The length 414 may be 1, 2, 5, 10, 20, 50, 100, or more times the internal or nominal diameter of the valve.

The foregoing description of the subject matter has been presented for purposes of illustration and description. It is not intended to be exhaustive or to limit the subject matter to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments except insofar as limited by the prior art.

What is claimed is:

1. An apparatus comprising:
   a first ball valve having a first position being an open position, said open position having an internal diameter through which flow occurs when said first ball valve is in said first position, said first ball valve having a second position being a closed position, said internal diameter being a nominal diameter of an input pipe for said first ball valve;
   a second ball valve having a first position being an open position, said open position having an internal diameter through which flow occurs when said second ball valve is in said first position, said second ball valve having a second position being a closed position;
   said first ball valve and said second ball valve being configured such that when said first ball valve is in said first position, said second ball valve is in said second position;
   a mechanism that causes said first ball valve to change from said first position to said second position while said second ball valve changes from said second position to said first position;
   a first sampling port on said first ball valve that drains said internal diameter when said first ball valve is in said second position, said first sampling port being inoperable when said first ball valve is in said first position;
   a second sampling port on said first ball valve that pressurizes said internal diameter when said first ball valve is in said second position; and
   an inlet junction upstream from said first ball valve and said second ball valve, said inlet junction comprising an input connection and a first connection to said first ball valve and a second connection to said second ball valve.

2. The apparatus of claim 1, said internal diameter of said first ball valve being equal to said internal diameter of said second ball valve.

3. The apparatus of claim 2 further comprising:
an outlet junction downstream from said first ball valve and said second ball valve, said outlet junction comprising an outlet connection and a first connection to said first ball valve and a second connection to said second ball valve.

4. The apparatus of claim 3, said first ball valve and said second ball valve being mechanically coupled such that said first ball valve and said second ball valve open and close simultaneously.

5. The apparatus of claim 3, said first ball valve and said second ball valve being electronically controllable such that said first ball valve and said second ball valve open and close substantially simultaneously.

6. The apparatus of claim 3, said inlet junction having a length from said input junction to said first connection being at least 10 times said internal diameter.

7. The apparatus of claim 3, said inlet junction having a length from said input junction to said first connection being at least 50 times said internal diameter.

8. The apparatus of claim 3, said inlet junction having a length from said input junction to said first connection being at least 100 times said internal diameter.

9. The apparatus of claim 3 further comprising:
a third sampling port on said second ball valve that drains said internal diameter when said second ball valve is in said second position.

10. The apparatus of claim 3, said first sampling port being located on a lower portion of said first ball valve.

11. The apparatus of claim 3, said first ball valve being a trunnion ball valve.

12. The apparatus of claim 3 further comprising:
a mechanical mechanism that causes said first ball valve and said second ball valve to operate.

13. The apparatus of claim 12, said mechanical mechanism comprising a handle.

14. The apparatus of claim 3 further comprising:
an automated system for causing said first ball valve and said second ball valve to operate.

15. The apparatus of claim 14, said automated system comprising a hydraulic actuator.

16. The apparatus of claim 14, said automated system comprising a pneumatic actuator.

17. The apparatus of claim 1 further comprising a temperature sensor.

18. The apparatus of claim 1 further comprising a pressure sensor.

19. The apparatus of claim 1 further comprising:
a lower reservoir connected to said first sampling port; and
an upper reservoir connected to said second sampling port.

* * * * *